United States Patent [19]
Shiner

[11] Patent Number: 5,993,212
[45] Date of Patent: Nov. 30, 1999

[54] MAGNETIC DEVICE PREVENTING DETACHMENT OF A DENTAL PROSTHESIS FROM A SUPPORT MEMBER IMPLANTED IN THE JAW

[76] Inventor: James R. Shiner, 3415 Lark St., San Diego, Calif. 92103

[21] Appl. No.: 09/189,650

[22] Filed: Nov. 10, 1998

[51] Int. Cl.⁶ ............... A61C 13/235; A61C 13/12
[52] U.S. Cl. .................... 433/172; 433/172
[58] Field of Search .................. 433/172, 173, 433/189

[56] References Cited

U.S. PATENT DOCUMENTS

| | | | |
|---|---|---|---|
| 4,184,252 | 1/1980 | Krol et al. | 433/189 |
| 4,209,905 | 7/1980 | Gillings | 433/189 |
| 4,508,507 | 4/1985 | Jackson | 433/189 |
| 4,626,213 | 12/1986 | Shiner et al. | 433/173 |
| 4,957,438 | 9/1990 | Bax | 433/189 |
| 4,975,059 | 12/1990 | Sendax | 433/189 |
| 4,993,950 | 2/1991 | Mensor, Jr. | 433/173 |
| 5,092,770 | 3/1992 | Zakula | 433/172 |
| 5,417,570 | 5/1995 | Zuest et al. | 433/172 |

*Primary Examiner*—John J. Wilson
*Assistant Examiner*—Patrick A. Hilsmier
*Attorney, Agent, or Firm*—Juettner Pyle & Piontek

[57] ABSTRACT

A denture retaining unit comprises a ball and socket structure, the socket being adapted for incorporation into a denture. The ball is a truncated sphere providing a flat face for magnetic engagement with a flat face of a magnetizable keeper, which keeper is adapted to be secured to a support member extending from the jaw. The unit permits lateral and/or angular movement between the denture in which the socket is embedded and the keeper, while the flat faces of the keeper and the sphere remain fully magnetically engaged. The sphere and the keeper have interengaging portions for limiting lateral movement therebetween and for preventing disengagement of the flat faces of the keeper and the sphere.

8 Claims, 1 Drawing Sheet

MAGNETIC DEVICE PREVENTING DETACHMENT OF A DENTAL PROSTHESIS FROM A SUPPORT MEMBER IMPLANTED IN THE JAW

TECHNICAL FIELD

The present invention relates to dental appliances, and more particularly to appliances which employ magnetic retention means. The invention is, in particular, an improvement on the dental appliance of U.S. Pat. No. 4,626,213, issued Dec. 2, 1986.

BACKGROUND

U.S. Pat. No. 4,626,213, the disclosure of which is incorporated herein by reference, discloses a magnetic denture retaining unit comprising a ball and socket structure and a magnetizable keeper. The socket is adapted for incorporation into a denture. The ball is a permanently magnetized truncated sphere providing a flat base adapted for magnetic engagement with a flat face on the keeper. The keeper is adapted to be secured to a support member extending from the jaw of the wearer, such as a tooth or tooth piece or root, or an implant or shank replacing the tooth. The ball is mounted for oscillatory or swiveling movement within the socket so as to maintain the flat base of the magnetic sphere in full face-to-face contact with the flat face of the magnetizable keeper whenever an unsupported portion of the denture is stressed, either angularly or with a lateral displacing force, without substantial simultaneous stress being applied to the tooth piece or implant.

However, in some cases, the act of mastication or articulation of the jaw is of such magnitude that the denture is displaced laterally from the keeper to such extent that the magnetic grip of the magnet on the keeper is lost and the denture becomes disassociated from the keeper and free to move about in the mouth of the wearer. For use in such cases, it would be desirable to provide some means for preventing excessive lateral displacement of the magnet relative to the keeper so as to maintain the magnet in denture retaining relationship to the keeper.

U.S. Pat. No. 4,993,950 discloses, in FIG. 11, a magnet with a skirt that surrounds the upper portion of the keeper to prevent or limit lateral movement of the denture on the keeper. However, this arrangement requires the keeper to protrude from the keeper support and the patient's gum line, which is a source of irritation when the denture is not in place.

SUMMARY OF THE INVENTION

The object of the present invention is to equip the dental appliance of U.S. Pat. No. 4,626,213 with means for preventing excessive lateral displacement of the denture relative to its keeper, and disassociation of the denture from the keeper, without sacrificing any of the benefits of the ball and socket structure of said patent and without adding materially to the cost of the appliance.

Another object is to equip the dental appliance of U.S. Pat. No. 4,626,213 with means for preventing excessive lateral placement of the denture relative to its keeper without incurring the disadvantages of the arrangement disclosed in U.S. Pat. No. 4,993,950.

In accordance with the present invention, excessive lateral movement of the ball and socket structure relative to the keeper is prevented by forming a cylindrical recess in the flat face of the keeper and a mating cylindrical projection on the flat base face of the permanently magnetized ball or sphere. With the cylindrical projection fitting conformably within the cylindrical recess, limited or controlled lateral movement is permitted and the ball is free to oscillate or swivel within its socket to maintain face-to-face contact between the flat end face of the projection and the flat base face of the recess. Consequently, all of the benefits and advantages of the ball and socket are retained and, at the same time, excessive lateral displacement is prohibited.

A particular advantage of the resultant structure resides in the ability of the socket mounted spherical magnet to attain flat face-to-face magnetic engagement between the base of the keeper recess and the base of the projection on the sphere despite angular variations in the placement of the keeper on the keeper support and of the socket ring in the denture. This is especially advantageous when a number of the magnetic retainers are required to hold a large denture in place in the patient's mouth.

These and other objects and advantages of the invention will become apparent from the following detailed description, as considered in conjunction with the accompanying drawings.

DETAILED DESCRIPTION OF A PREFERRED EMBODIMENT

The following is a detailed description of an embodiment of the invention presently deemed by the inventor to be the best mode of carrying out his invention.

Figure 1:
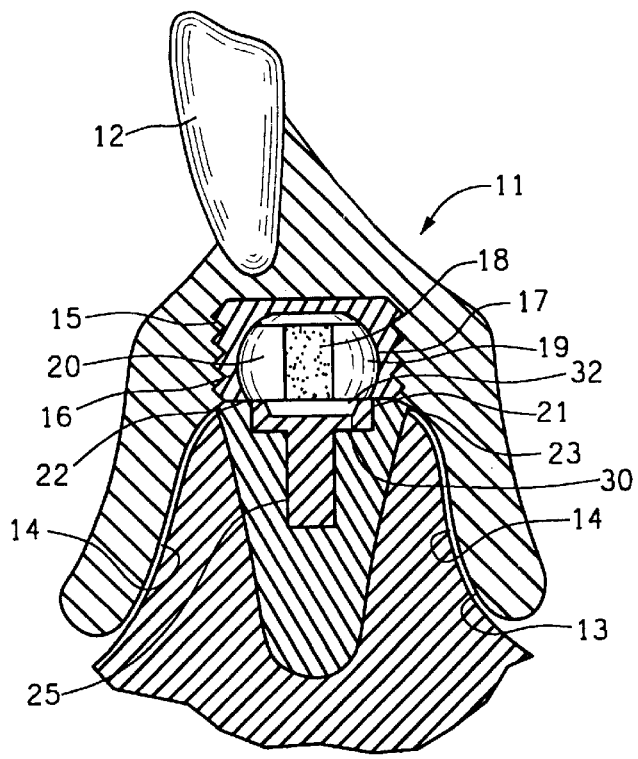
FIG. 1 is a vertical section of a preferred embodiment of the dental appliance of the invention as installed in a patient's mouth.

Referring to FIG. 1, the magnetic denture retention unit of the invention can be considered as being formed of a first sub-unit and a second sub-unit. The first sub-unit is further described as follows: An overdenture 11, having an artificial tooth 12 embedded therein, and having a gum tissue conforming surface 13 on the underside thereof, is positioned over the natural gums 14 of a denture wearer. A threaded cavity 15 extends inwardly of the overdenture 11 for threadably receiving socket ring 16, the socket ring 16 being dimensioned to receive and support magnetic member 17, comprising a bar magnet 18 and magnetizable leg element 19 and 20, together forming a truncated ball or sphere. Magnetic forces emanating from the magnetic member 17 function to retain the denture 11 in place upon the gums 14 as a result of magnetic attachment to a second sub-unit which includes a magnetizable keeper element 21, which is secured to a support member 22. Support member 22 may take various forms such, for example, as a dental implant mounted for support by the denture wearer's jaw bone. In providing such implant, illustratively, the tooth or teeth are after suitable treatment amputated to a level which is above the gum ridge 23, and then drilled to provide a recess for conformably accommodating a shank portion 25 which is integral with the keeper element 21 and extends downwardly therefrom.

The magnet 18 preferably comprises cobalt and a rare earth metal, and the sphere segments 19–20 and keeper 21 ferromagnetic stainless steel.

The face of magnet member 17 projects slightly outside the socket ring 16 and has a flat face or base for engagement with a flat face on the exposed surface of the keeper element 21. The magnetic attraction between the magnet element 17 and keeper element 21 retains the denture 11 in position on the gums 14 of the denture wearer.

The magnetic ball or sphere 17 is mounted for oscillation or swiveling movement in the socket ring 16 for universal oscillatory movement through an arc, preferably in the order of about 20 degrees in all directions, i.e, front to rear, side to side, and diagonally relative to the gums of the wearer. Consequently, the flat face of the magnet element 17 will in most instances be magnetically engaged in flat face-to-face engagement with the exposed flat surface of the keeper 21, irrespective of relative lateral movement and irrespective of angular displacement.

In particular, the application of a lateral force on the overdenture 11 permits relative movement of the overdenture 11 with respect to the keeper 21 while maintaining full magnetic contact between the flat face of the keeper 21 and the corresponding flat face of the magnet member 17, thereby substantially minimizing the destructive action otherwise exerted on the amputated tooth or the implant post which ordinarily occurs when lateral or angular forces are imposed on the denture 11. However, in some cases, the act of mastication or other articulation of the jaw of the denture wearer causes such extreme lateral movement of the overdenture 11 relative to the keeper 21 as to cause the magnet 17 to be physically and magnetically separated from the keeper whereupon the denture is disassociated from the keeper and free to move about in the mouth of the wearer.

For use in such cases, the present invention incorporates into the dental appliance means for preventing lateral disassociation of the magnetic element 17 from the keeper element 21 while still maintaining the benefits and advantages of the oscillatory movement accommodated by the ball and socket mounting of the truncated magnetic ball or sphere 17.

Figure 2:
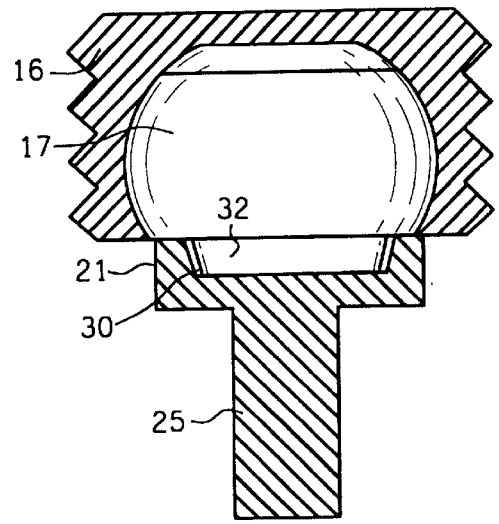
FIG. 2 is a vertical section of the ball and socket structure and keeper element of the preferred embodiment of the invention.
Figure 3:
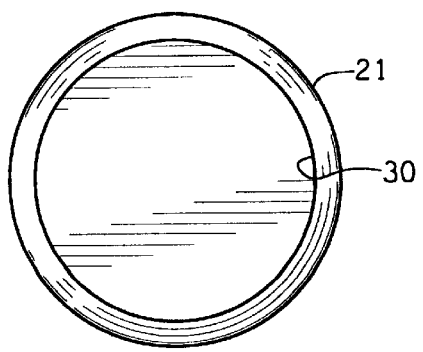
FIG. 3 is a top plan view of the keeper element illustrated in FIG. 2.

As illustrated in the drawings, a cylindrical recess 30 having a flat bottom face is formed in the exposed face of the keeper element 21 and a complementary cylindrical flat faced mating projection 32 is provided on the base of the ball or sphere 17. With the projection 32 fitted within the recess 30, the side wall of the recess 30 prevents excessive lateral movement of the projection 32 and thus prevents lateral disassociation of the denture 11 from the keeper 21. Preferably, as illustrated in FIG. 2, the side walls of the recess and the projection are slightly tapered and have a lateral tolerance or clearance so as to facilitate entry of the projection completely into the recess so that the flat face of the projection may engage flush against the flat bottom face of the recess and provide maximum magnetic retention of the denture on the keeper. Also, this accommodates a limited degree of lateral movement between the denture and the keeper to insure proper functioning of the magnetic ball. As an alternative arrangement, the recess could be provided in the magnetic element and the projection on the keeper element. However, this is not the preferred arrangement. In the preferred arrangement, as illustrated in FIG. 1, the upper margin of the keeper 21 does not protrude into the mouth when the denture is removed.

The objects and advantages of the invention have therefore been shown to be attained in a convenient, practical, economical and facile manner.

While a preferred embodiment of the invention has been herein illustrated and described, it is to be appreciated that various changes, rearrangements and modifications may be made therein without departing from the scope of the invention as defined by the appended claims.

What is claimed is:

1. A denture retaining unit comprising a first subunit in the form of a ball and socket structure wherein said structure comprises a socket ring which is adapted to receive and house the ball and to be incorporated into a denture, and the ball is in the form of a truncated sphere and comprised of a permanent magnet, and a second subunit in the form a flat faced magnetizable keeper adapted to be secured to a support member extending from the jaw inside the mouth; said truncated sphere having a flat face for magnetic engagement with the flat face of the magnetizable keeper;

one of said flat faces having a cylindrical recess therein and the other of said flat faces having a complementary cylindrical projection thereon for mating engagement within said recess for limiting lateral movement of said sphere relative to said keeper and for preventing lateral disassociation of said first subunit from said second subunit.

2. A denture retaining unit as set forth in claim 1 wherein said cylindrical recess has a flat bottom face and said cylindrical projection has a flat end face for face-to-face flush engagement with one another.

3. A denture retaining unit as set forth in claim 1 wherein said recess and said projection have clearance therebetween for accommodating limited lateral movement of said first subunit relative to said second subunit.

4. A denture retaining unit as set forth in claim 3 wherein said sphere projects out of said socket sufficiently to permit oscillation of the sphere without separation of the face-to-face engagement of the flat faces of said sphere and said keeper during relative lateral movement between said subunits.

5. A denture retaining unit as set forth in claim 1 wherein said recess is in said keeper.

6. A denture retaining unit comprising a first subunit in the form of a ball and socket structure wherein said structure comprises a socket ring which is adapted to receive and house the ball and to be incorporated into a denture, and the ball is in the form of a truncated sphere and comprised of a permanent magnet, and a second subunit in the form of a flat faced magnetizable keeper adapted to be secured to a support member extending from the jaw inside the mouth, said truncated sphere having a flat face for magnetic engagement with the flat face of the magnetizable keeper;

said sphere projecting out of said socket sufficiently to permit oscillation of the sphere without separation of the face-to-face engagement of the flat faces of said sphere and said keeper, the flat face of said keeper having a cylindrical recess therein, the flat face of said sphere having a complementary cylindrical projection thereon for mating engagement within said recess for limiting lateral movement of said sphere relative to said keeper and for preventing lateral disassociation of said first subunit from said second subunit.

7. A denture retaining unit as set forth in claim 6 wherein said cylindrical recess has a flat bottom face and said cylindrical projection has a flat end face for face-to-face flush engagement with one another.

8. A denture retaining unit as set forth in claim 6 wherein said recess and said projection have clearance therebetween for accommodating limited lateral movement of said first subunit relative to said second subunit, said sphere accommodating such relative movement without separation of the face-to-face magnetic engagement of said sphere with said keeper.

* * * * *